(12) United States Patent
Balloni et al.

(10) Patent No.: US 6,725,077 B1
(45) Date of Patent: Apr. 20, 2004

(54) APPARATUS AND METHOD FOR JUST-IN-TIME LOCALIZATION IMAGE ACQUISITION

(75) Inventors: William J. Balloni, Menomonee Falls, WI (US); Kristine L. Gould, Delafield, WI (US); Yawar Murad, Milwaukee, WI (US); Bipin Salunkhe, Pewaukee, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 596 days.

(21) Appl. No.: 09/752,055

(22) Filed: Dec. 29, 2000

(51) Int. Cl.$^7$ ................................................. A61B 5/05
(52) U.S. Cl. ..................................................... 600/410
(58) Field of Search ............................... 600/410, 411, 600/412, 413, 414, 415, 416, 417, 423, 436; 436/173; 324/307, 308, 309

(56) References Cited

U.S. PATENT DOCUMENTS

| | | | | |
|---|---|---|---|---|
| 5,124,650 A | * | 6/1992 | Granot ........................ | 324/309 |
| 5,233,299 A | | 8/1993 | Souza et al. ................. | 324/307 |
| 5,402,337 A | * | 3/1995 | Nishide ....................... | 345/426 |
| 5,447,155 A | * | 9/1995 | NessAiver et al. .......... | 600/410 |
| 5,526,812 A | * | 6/1996 | Dumoulin et al. ........... | 600/407 |
| 5,594,844 A | * | 1/1997 | Sakai et al. .................. | 345/427 |
| 5,709,208 A | * | 1/1998 | Posse et al. ................. | 600/410 |
| 5,833,609 A | * | 11/1998 | Dannels et al. ............. | 600/410 |
| 5,842,989 A | * | 12/1998 | Zur .............................. | 600/410 |
| 5,881,728 A | * | 3/1999 | Mistretta et al. ............ | 600/420 |
| 6,061,420 A | * | 5/2000 | Strong et al. ................ | 378/4 |
| 6,123,733 A | * | 9/2000 | Dalton ......................... | 703/5 |
| 6,211,674 B1 | * | 4/2001 | Cline et al. .................. | 324/307 |
| 6,519,354 B1 | * | 2/2003 | Oshio .......................... | 382/130 |

* cited by examiner

*Primary Examiner*—Daniel Robinson
(74) *Attorney, Agent, or Firm*—Foley & Lardner; Peter J. Vogel; Michael A. Della Penna (57) ABSTRACT

A method and apparatus for providing a "just-in-time" localizer image of an object of interest from which a high resolution image can be based is disclosed herein. The "just-in-time" localizer image is acquired based on at least one of a default localizer image of the object of interest, a precursor image of the object of interest, and a representation of a three-dimensional volume data set associated with the object of interest. The "just-in-time" localizer image and the high resolution image are prescribed, acquired, and displayed within a single graphical prescription environment.

26 Claims, 10 Drawing Sheets

APPARATUS AND METHOD FOR JUST-IN-TIME LOCALIZATION IMAGE ACQUISITION

BACKGROUND OF THE INVENTION

The present invention relates generally to imaging systems. More particularly, the present invention relates to an imaging system configured to provide prescriptible images on an as-need basis in a streamlined prescription environment.

In order to obtain clinically useful images of a region of interest of a subject (e.g., a particular anatomy of a patient) using an imaging system (e.g., a magnetic resonance (MR) imaging system), an operator of the imaging system will typically acquire two types of images—localizer images and target images. Because each patient's anatomy is unique, a patient's position relative to the imaging system and/or the exact location of his/her injury, defect, or disease may vary from one patient to another. Hence, it may not be possible for the operator to acquire exactly desired images of an actual region of interest without a point of reference (e.g., a localizer image).

Localizer images (also referred to as scout images) provide an educated starting point from which target images (i.e., desired images of the actual region of interest for purpose of medical diagnosis) can be prescribed. In some cases, localizer images may even be comparable to a trial acquisition of target images to be acquired. Localizer images comprise images of relatively low resolution in comparison with target images, and may be images having an image acquisition or scan plane only in the general vicinity of where the actual region of interest may be. The operator uses preset or default prescription parameters, or a quick prescription of the general region of the patient to be imaged, to relatively quickly acquire such localizer images.

Once localizer images have been acquired, the operator views the localizer images to specify acquisition parameters for the target images to be acquired. The orientations and locations of the scan planes associated with the target images are prescribed relative to the orientation and location of the localizer images. Using localizer images to generate the desired target images reduces overall scan time, both the average scan time per image and the number of high resolution images that are ultimately deemed to be undesirable.

In conventional systems, localizer images, typically organized as a set or series of localizer images, are acquired in a first prescription or acquisition environment included in the imaging system and such localizer images are then stored in a memory or storage device. These stored localizer images are loaded into a second prescription or acquisition environment to prescribe target images therefrom. Different prescription environments are utilized, because, among other things, the resolution of localizer and target images differ enough that their acquisition process (including the prescription and/or tools associated therewith) also differs.

Unfortunately, utilizing a plurality of prescription environments is time consuming and cumbersome. Moreover, the operator may determine that the localizer images being viewed in the second prescription environment (i.e., the target image prescription environment) are not useful, for example, he/she is unable to determine where the actual region of interest is relative to the displayed localizer images. In this case, the operator either prescribes and commits to target images that may or may not image the actual region of interest, or he/she must return to the first prescription environment (i.e., the localizer image prescription environment) to acquire new localizer images and then return to the second prescription environment.

Thus, there is a need for an apparatus and method for localizer and target image prescription and/or acquisition in a single prescription environment. There is a further need for an apparatus and method for only acquiring specific localizer images as needed in real-time, rather than pre-acquiring all localizer images in order for target image prescription to commence.

BRIEF SUMMARY OF THE INVENTION

One embodiment of the invention relates to a method for generating a clinically useful image having a desired image acquisition plane in a short time frame. The method includes prescribing a second image relative to at least one of a default second image, a first image, and a representation of a three-dimensional volume data set. The method further includes acquiring the second image, displaying the second image, and prescribing the clinically useful image relative to the second image. The method still further includes acquiring the clinically useful image, and displaying the clinically useful image. The second image and the clinically useful image are prescribed, acquired, and displayed within a single graphical prescription environment included in an imaging system.

Another embodiment of the invention relates to an imaging system for generating a clinically useful image having a desired image acquisition plane in a short time frame. The system includes means for prescribing a second image relative to at least one of a default second image, a first image, and a representation of a three-dimensional volume data set. The system further includes means for acquiring the second image, means for displaying the second image, and means for prescribing the clinically useful image relative to the second image. The system still further includes means for acquiring the clinically useful image, and means for displaying the clinically useful image. The second image and the clinically useful image are prescribed, acquired, and displayed within a single graphical prescription environment included in the imaging system.

Still another embodiment of the invention relates to a localizer image generated by providing a first image on a graphical user interface, and prescribing the localizer image based on the first image on the graphical user interface. The localizer image is further generated by providing the localizer image on the graphical user interface. The first image is selected from a group including a precursor image, a default image, and a representation of a three-dimensional volume data set. A localization image acquisition plane is associated with the localizer image. The localizer image is suitably configured to plan a clinically useful image on the graphical user interface, a clinically useful image acquisition plane associated with the clinically useful image and the localization image acquisition plane bearing a relationship to each other.

BRIEF DESCRIPTION OF THE DRAWINGS

The preferred embodiment will become more fully understood from the following detailed description, taken in conjunction with the accompanying drawings, wherein like reference numerals denote like elements, in which.

DETAILED DESCRIPTION OF THE EXEMPLARY EMBODIMENTS

Figure 1:
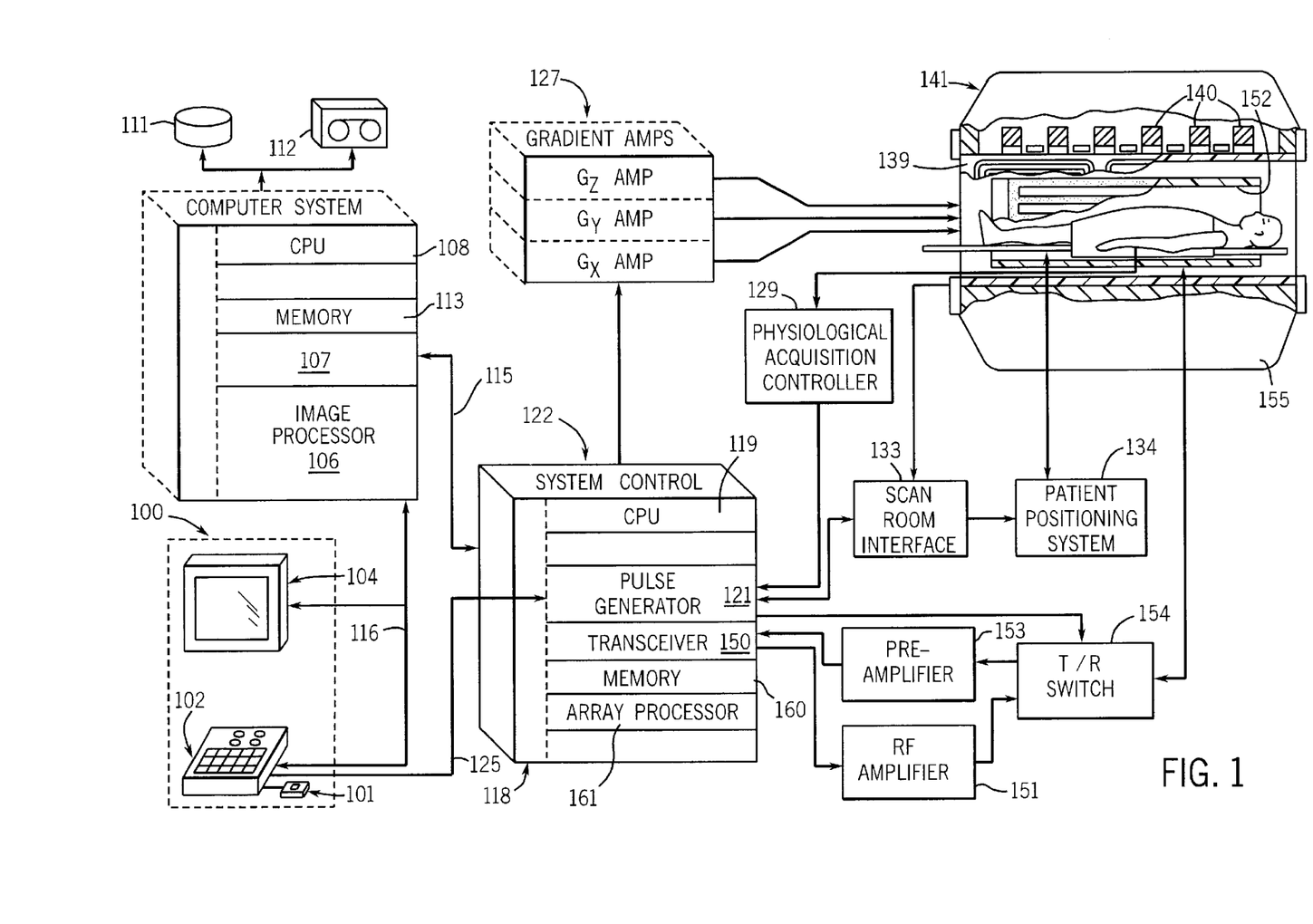
FIG. 1 is a block diagram of a magnetic resonance (MR) imaging system which employs an embodiment of the present invention.

Referring to FIG. 1, there is shown the major components of a magnetic resonance (MR) imaging system. The operation of the system is controlled from an operator console 100 which includes an input device 101, a control panel 102, and a display 104. Console 100 communicates through a link 116 with a separate computer system 107 that enables an operator to control the production and display of images on screen 104. Computer system 107 includes a number of modules which communicate with each other through a backplane. These include an image processor module 106, a CPU module 108, and a memory module 113, known in the art as a frame buffer for storing image data arrays. Computer system 107 is linked to a disk storage 111 and a tape drive 112 for storage of image data and programs, and it communicates with a separate system control 122 through a high speed serial link 115.

System control 122 includes a set of modules connected together by a backplane. These include an CPU module 119 and a pulse generator module 121 which connects to operator console 100 through a serial link 125. It is through this link 125 that system control 122 receives commands from the operator which indicate the scan sequence that is to be performed. Pulse generator module 121 operates the system components to carry out the desired scan sequence. It produces data which indicate the timing, strength and shape of radio frequency (RF) pulses, and the timing and length of a data acquisition window. Pulse generator module 121 connects to a set of gradient amplifiers 127, to control the timing and shape of the gradient pulses to be produced during the scan. Pulse generator module 121 also receives patient data from a physiological acquisition controller 129 that receives signals from a number of different sensors connected to the patient, such as ECG signals from electrodes or respiratory signals from a bellows. And finally, pulse generator module 121 connects to a scan room interface circuit 133 which receives signals from various sensors associated with the condition of the patient and the magnet system. It is also through scan room interface circuit 133 that a patient positioning system 134 receives commands to move the patient to the desired position for the scan.

The gradient waveforms produced by pulse generator module 121 are applied to a gradient amplifier system 127 comprised of $G_x$, $G_y$, and $G_z$ amplifiers. Each gradient amplifier excites a corresponding gradient coil in an assembly generally designated 139 to produce magnetic field gradients used for spatially encoding acquired signals. Gradient coil assembly 139 forms part of a magnet assembly 141 which includes a polarizing magnet 140 and a whole-body RF coil 152.

Although assembly 139 is shown as a closed magnet structure, it should be understood that assembly 139 may be an open magnet structure and a separate surface RF coil may be provided to act as a localized receiver coil.

A transceiver module 150 in system control 122 produces pulses which are amplified by an RF amplifier 151 and coupled to RF coil 152 by a transmit/receiver switch 154. The resulting signals emitted by the excited nuclei in the patient may be sensed by RF coil 152 and coupled through transmit/receive switch 154 to a preamplifier 153. The amplified MR signals are demodulated, filtered, and digitized in the receiver section of transceiver 150. Transmit/receive switch 154 is controlled by a signal from pulse generator module 121 to electrically connect RF amplifier 151 to RF coil 152 during the transmit mode and to connect preamplifier 153 during the receive mode. Transmit/receive switch 154 also enables a separate RF coil (for example, a head coil or a surface coil) to be used in either the transmit or receive mode.

MR signals picked up by RF coil 152 are digitized by transceiver module 150 and transferred to a memory module 160 in system control 122. When the scan is completed and an entire array of data has been acquired in memory module 160, an array processor 161 operates to Fourier transform the data into an array of image data. The image data are conveyed through serial link 115 to computer system 107 where they are stored in disk memory 111. In response to commands received from operator console 100, these image data may be archived on tape drive 112, or they may be further processed by image processor 106 and conveyed to operator console 100 and presented on display 104.

Figure 2:
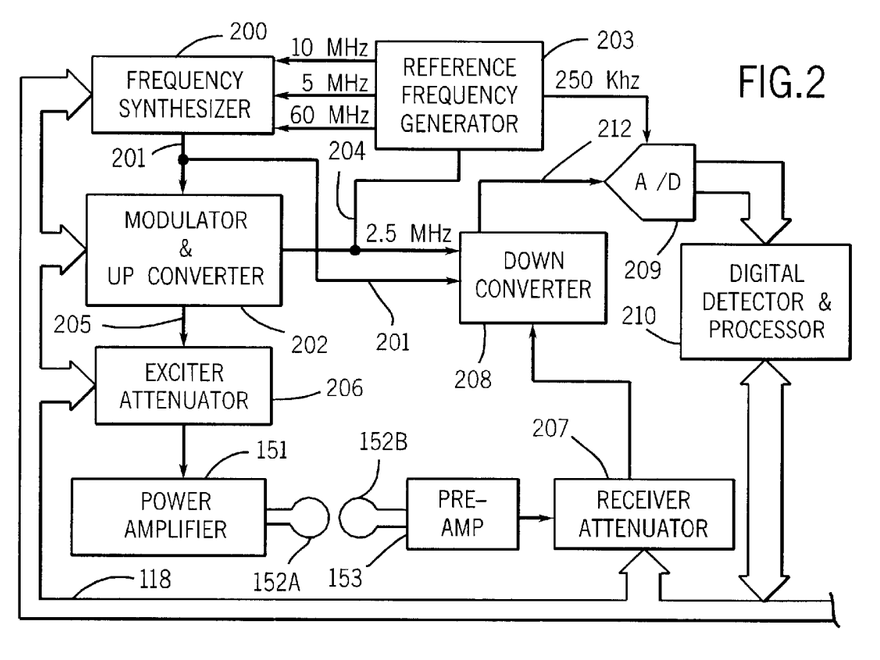
FIG. 2 is an electrical block diagram of a transceiver block which forms part of the MR imaging system of FIG. 1.

Referring particularly to FIGS. 1 and 2, transceiver 150 produces the RF excitation field $B_1$ through power amplifier 151 at a coil 152A and receives the resulting signal induced in a coil 152B. As indicated above, coils 152A and 152B may be separate as shown in FIG. 2, or they may be a single wholebody coil as shown in FIG. 1. The base, or carrier, frequency of the RF excitation field is produced under control of a frequency synthesizer 200 which receives a set of digital signals from CPU module 119 and pulse generator module 121. These digital signals indicate the frequency and phase of the RF carrier signal produced at an output 201. The commanded RF carrier is applied to a modulator and up converter 202 where its amplitude is modulated in response to a signal R(t) also received from pulse generator module 121. Signal R(t) defines the envelope of the RF excitation pulse to be produced and is produced in module 121 by sequentially reading out a series of stored digital values. These stored digital values may, in turn, be changed from operator console 100 to enable any desired RF pulse envelope to be produced.

The magnitude of the RF excitation pulse produced at output 205 is attenuated by an exciter attenuator circuit 206 which receives a digital command from backplane 118. The attenuated RF excitation pulses are applied to power amplifier 151 that drives RF coil 152A.

Referring still to FIGS. 1 and 2, the MR signal produced by the subject is picked up by receiver coil 152B and applied through preamplifier 153 to the input of a receiver attenuator 207. Receiver attenuator 207 further amplifies the signal by an amount determined by a digital attenuation signal received from backplane 118.

The received signal is at or around the Larmor frequency, and this high frequency signal is down converted in a two step process by a down converter 208 which first mixes the MR signal with the carrier signal on line 201 and then mixes the resulting difference signal with the 2.5 MHz reference signal on line 204. The down converted MR signal is applied to the input of an analog-to-digital (A/D) converter 209 which samples and digitizes the analog signal and applies it to a digital detector and signal processor 210, which produces 16 bit in-phase (I) values and 16-bit quadrature (Q) values corresponding to the received signal. The resulting stream of digitized I and Q values of the received signal are outputted through backplane 118 to memory module 160 where they are normalized and then employed to reconstruct an image.

Figure 3:
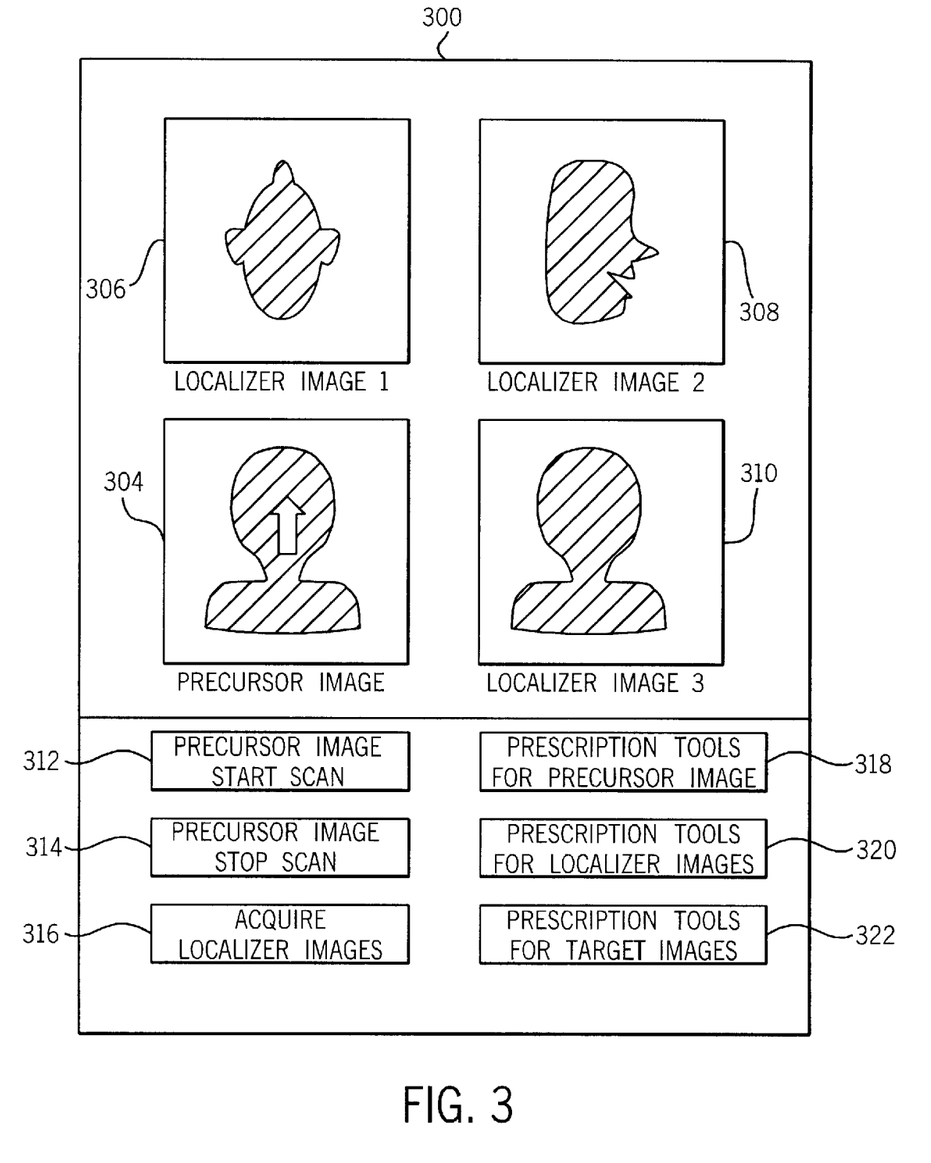
FIG. 3 is a portion of one embodiment of a graphical user interface included in the MR imaging system of FIG. 1.
Figure 4:
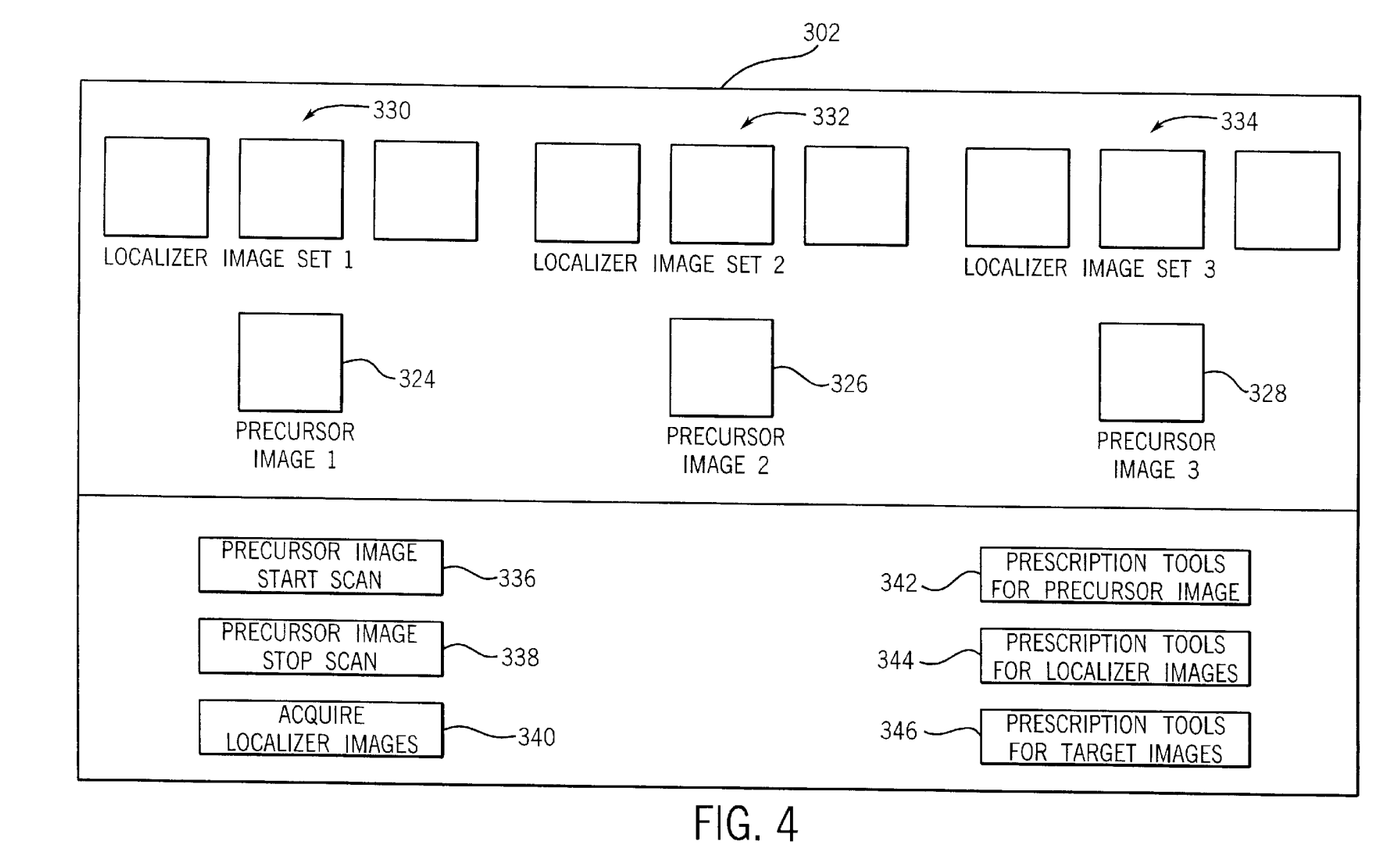
FIG. 4 is a portion of another embodiment of a graphical user interface included in the MR imaging system of FIG. 1.

In one embodiment, an operator (e.g., a technician, a physician, etc.) interfaces with the MR imaging system via operator console 100 (also referred to as an operator interface). Input device 101 of operator console 100 can be, but is not limited to, a mouse, a joystick, a keyboard, a trackball, a touch screen, a light wand, a voice controller, or a platform-mounted spatial manipulation device (such as a Spaceball™ manufactured by Spacetec, Inc. of Lowell, Massachusetts). Display 104 (also referred to as an electronic display) of operator console 100 preferably displays a graphical user interface (GUI), such as a graphical user interface (GUI) 300 or a graphical user interface (GUI) 302. GUIs 300, 302, among others, displays one or more MR images and icons to manipulate such MR images and the MR imaging system.

Referring to FIG. 3, GUI 300 includes a precursor image window 304, a first localizer image window 306, a second localizer image window 308, a third localizer image window 310, a precursor image start scan icon 312, a precursor image stop scan icon 314, an acquire localizer images icon 316, a prescription tools for precursor image icon 318, a prescription tools for localizer image icon 320, and a prescription tools for target images icon 322. GUI 300 is configured to permit the operator to accurately prescribe useful localizer images and to acquire such localizer images only as needed (i.e., "just-in-time" localizer or localizer images), from which desirable target images may be prescribed. GUI 300 is further configured to permit the operator to prescribe or plan desirable target images in the same graphic prescription environment from which localizer images were prescribed, acquired, and displayed.

Referring to FIG. 4, GUI 302 includes a first precursor image window 324, a second precursor image window 326, a third precursor image window 328, a set of first localizer images windows 330, a set of second localizer images windows 332, a set of third localizer images windows 334, a precursor image start scan icon 336, a precursor image stop scan icon 338, an acquire localizer images icon 340, a prescription tools for precursor image icon 342, a prescription tools for localizer images icon 344, and a prescription tools for target images icon 346. GUI 302 is also configured to permit the operator to accurately prescribe useful localizer images and to acquire such localizer images only as needed. GUI 302 is further configured to permit the operator to prescribe and/or acquire desirable target images from the same environment. GUI 302, as shown in FIG. 4, is an environment configured to simultaneously handle three sets of images, each set relating to a precursor image and its corresponding localizer images.

It should be understood that GUIs 300 and 302 are offered for illustrative purposes only and that the MR imaging system may provide a variety of other GUIs, such as, GUIs having a different layout or functionality than GUIs 300 or 302. For example, the configuration of each of GUI 300 or 302 may be modified based on operator or user preferences, such as, having more or less than three localizer images associated with a given precursor image or customizing various icons for prescription, acquisition, and display of the images.

Localizer images (also referred to as localizer images) are preferably two-dimensional (2-D) MR images that are acquired to serve as a reference frame or starting point from which final or actually desired MR images (hereinafter referred to as target images) may be prescribed. Localizer images typically have an acquisition time less than 30 seconds, in contrast to target images which have an acquisition time on the order of 30 seconds to 30 minutes. Target images are preferably of equal or higher image quality than localizer images because resolution, image contrast, and other image quality factors are relevant in the clinical usefulness of such images, e.g., for a physician to provide accurate diagnosis and/or treatment of a disease, anatomy, etc.

Localizer images permit a region of interest of a subject being imaged (such as a particular anatomy of a patient) to be visualized relatively quickly, such that the operator may get orientated within the 3-D space of the patient and/or to locate the desired region of interest within the patient to be further imaged. Localizer images also provide a reference frame or image from which location, orientation, and other imaging parameters associated with one or more target images to be subsequently acquired can be prescribed. For example, a scanning position (i.e., the location and orientation of an image acquisition or scan plane) of a target image is preferably prescribed from one or more localizer images. In another example, a saturation band location associated with a target image may be prescribed using a localizer image. In still another example, a motion reducing reference location (i.e., defining a marker relative to an anatomy to trigger image acquisition only when that anatomy is in approximately the same location relative to the marker such that image acquisition occurs at approximately the same point in a cycle, such as the breathing cycle) may also be prescribed for a target image.

In FIG. 3, window 304 displays a precursor image. Windows 306, 308, 310 display a first localizer image, a second localizer image, and a third localizer image, respectively. In one embodiment, scan planes associated with first, second, and third localizer images are mutually orthogonal to each other and are preferably axial, sagittal, and coronal cross-sections (for example, the orthogonal images of a patient's head shown in windows 306–310).

Alternatively, localizer images shown in windows 306–310 may be orthogonal to each other but not necessarily be at axial, sagittal, and coronal orientations. In still another embodiment, localizer images shown in windows 306–310 may be in an operator specified orientation, such as not being orthogonal to each other (e.g., being parallel to each other). In these cases, GUI 300 may provide prescription tools for the operator to specify orientations of a given set of localizer images with respect to each other. In still another alternative, GUI 300 may display more or less than three localizer images. For example, GUI 300 may only display one localizer image. Other details relating to GUI 300 will be discussed henceforth in relation to FIGS. 5–7.

Figure 5:
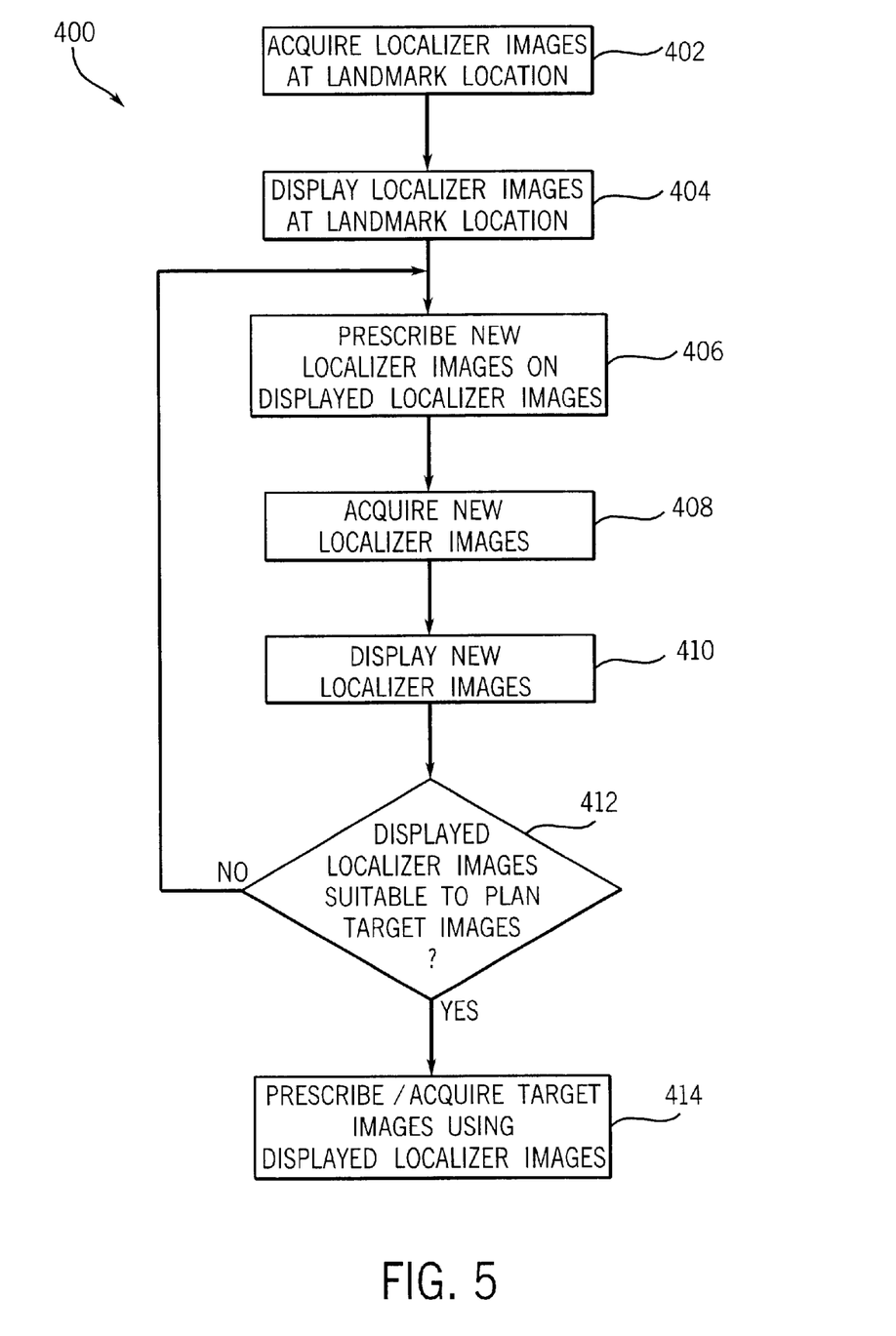
FIG. 5 is a flow diagram showing one embodiment of an image acquisition scheme included in the MR imaging system of FIG. 1.

Referring to FIG. 5, there is shown a flow diagram of one embodiment of a "just-in-time" localizer image acquisition scheme 400. Scheme 400 includes an acquire initial localizer images step 402, a display initial localizer images step 404, a prescribe new localizer images step 406, an acquire new localizer images step 408, a display new localizer images step 410, a suitability check step 412, and a plan target image step 414.

In step 402, initial localizer images (may be a single localizer image or a set of localizer images, such as orthogonal localizer images) are acquired at a landmark position within the subject of interest at a start of a scanning session. The landmark position is a default position provided by the MR imaging system or a default position based on the general region of the patient to be imaged. For example, if the region to be imaged is in the chest area, the chest landmark position could be the center of the chest. Then in step 404, the acquired initial localizer images are displayed at windows 306–310 of GUI 300. In the above example, such initial localizer images would show various cross-sectional views of approximately the center of the patient's chest.

In most instances, initial localizer images are unlikely to provide the desired view of the region of interest. Hence, step 406 permits the operator to prescribe the position of a new (or next) localizer image(s), relative to the currently displayed localizer images (e.g., initial localizer images). Prescription is preferably performed using one or more graphical prescription tools (not shown) provided on GUI 300. Graphical prescription tools, as well-known in the art, provide a variety of interactive functionality. Using a currently displayed image, the operator can graphically specify, among others, the position of the scan plane for the next image to be acquired. Graphical prescription tools include, but are not limited to, rotation, translation, magnification, resizing, etc.

Prescription can be initiated by moving a cursor displayed on GUI 300 (or otherwise pointing) to one of windows 306–310 containing an initial localizer image. This will automatically bring up graphical prescription tools with which to prescribe the new localizer image(s). Alternatively, the operator may "click" on icon 320 to avail him/herself of localizer image prescription tools. In any case, the operator prescribes a location (e.g., a (x, y, z) point within the patient) and/or an orientation (e.g., an angle or tilt of the next scan plane) of the next localizer images relative to the currently displayed localizer images (e.g., initial localizer images).

Once the operator has specified the imaging parameters for the next localizer images, such next localizer images are acquired (step 408) and displayed (step 410) in windows 306–310. The initial localizer images are discarded and are replaced with the next localizer images in windows 306–310. In one embodiment, prescribing the next localizer image from any of the initial localizer images provided on windows 306–310 causes updates (e.g., new or next localizer images) for all three windows 306–310. Presumably, none of the initial localizer images were particularly useful (since a new localizer image was requested in step 106) and updating windows 306–310 each time a new localizer image has been prescribed on any one of the initial localizer images ensures that the set of localizer images displayed on windows 306–310 at any given time are various cross-sectional views about a same location within the subject of interest.

Alternatively, prescriptions carried out on a given initial localizer image will only update that initial localizer image. For example, prescribing the next localizer image using the initial localizer image at window 306 will only cause one new localizer image to be acquired (step 408) and displayed (step 410) at window 306. The images displayed on windows 308, 310 would be uneffected.

If the operator finds one or more of the new localizer images to be suitable (e.g., the displayed localizer images contain desired image content) (step 412), then such new localizer images may be used to prescribe target images therefrom (step 414). Since such new localizer images already contain desired image content (in other words, the desired position of the subject of interest to be imaged has been identified), the scan plane positions of the target images may be approximately the same or identical to those of the new localizer images. Target images may also be displayed on a window of GUI 300 (not shown).

Otherwise, when the new localizer images are not suitable to prescribe the target images therefrom, the currently displayed localizer images are utilized to prescribe still another new localizer images (return to step 406). This loop may be repeated a plurality of time, as needed, until suitable localizer images are found.

Figure 6A:
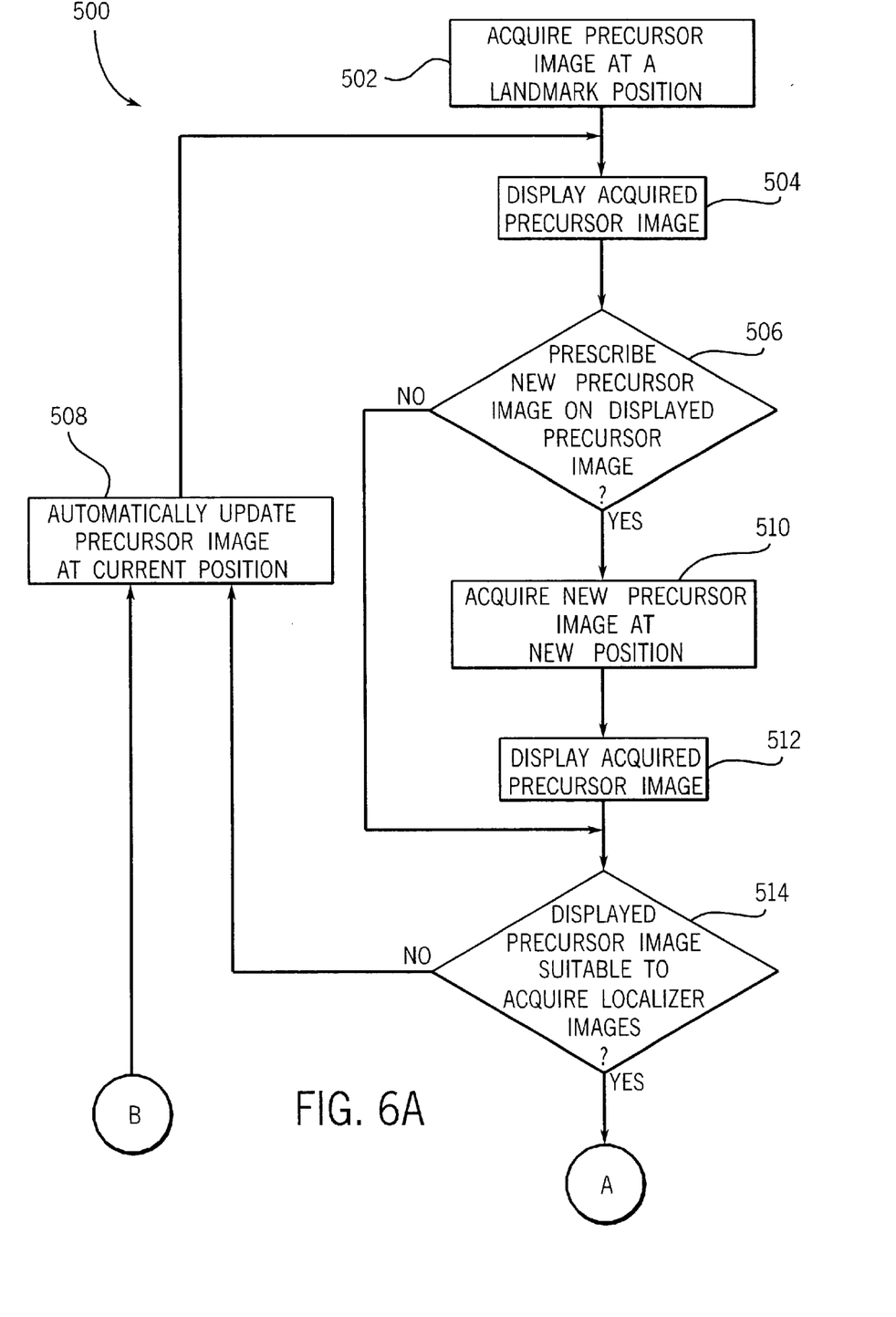
FIGS. 6A–6B are flow diagrams showing another embodiment of the image acquisition scheme included in the MR imaging system of FIG. 1.
Figure 6B:
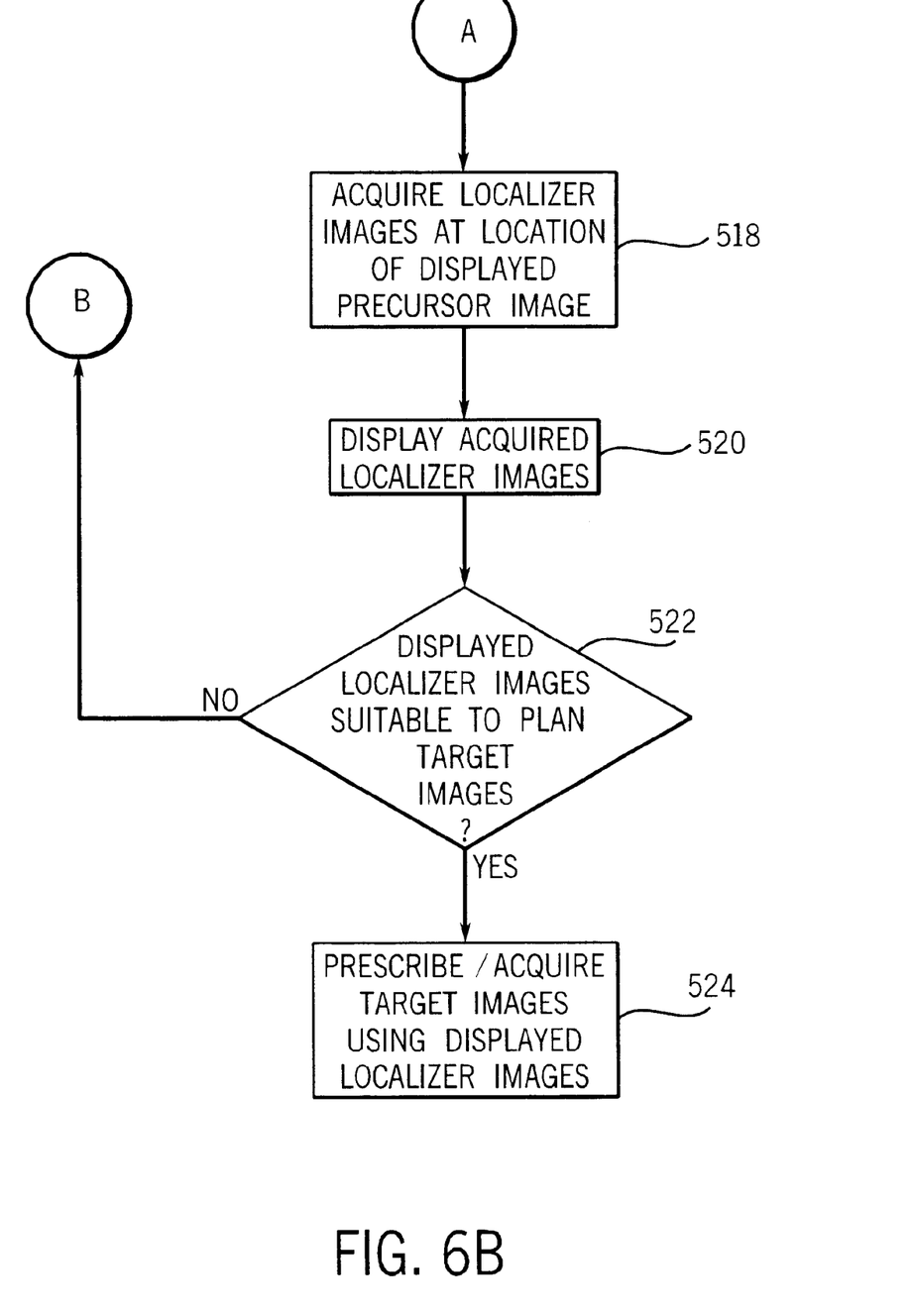

Referring to FIGS. 6A–6B, there is shown flow diagrams of another embodiment of a "just-in-time" localizer image acquisition scheme or methodology 500. Scheme 500 includes an acquire precursor image step 502, a display precursor image step 504, a precursor image suitability check step 506, an automatic precursor image update step 508, an acquire new precursor image step 510, a display new precursor image step 512, a new precursor image suitability check step 514, an acquire localizer images step 518, a display localizer images step 520, a localizer images suitability check step 522, and a plan target images step 524. Scheme 500 is configured to provide precursor images in real-time from which "just-in-time" localizer images may be obtained.

In step 502, a precursor image at a landmark position is acquired at the start of a scanning session. The operator may initiate such acquisition at the landmark position by clicking on icon 312. The precursor image is displayed at window 304 of GUI 300 (step 504). For example, window 304 shows a precursor image of a cross-sectional view of a patient's head. The precursor image is preferably a 2-D MR image acquired in real-time or quasi real-time as quickly as possible. The precursor image, also referred to as a real-time image, may have a lower resolution and/or a shorter acquisition time than any of the localizer images.

The MR imaging system is configured to continuously update the precursor image by repeatedly scanning at the last scan plane specified (e.g., providing a series of real-time precursor images at the landmark position). The operator views the precursor image(s) as they are provided on window 304, and when he/she sees that the image content is less than desirable (i.e., the scan plane of the precursor image is not at the desired location and orientation of the subject of interest to be imaged), then the operator prescribes (step 506) a new scan plane for a new or next precursor image to be acquired (step 510). Such prescription of the next precursor image is made relative to the current precursor image being displayed at window 304 (e.g., a graphical prescription). The prescription may be initiated by moving a cursor of sorts close to or into window 304 or by clicking icon 318 (similar to discussion above). In this manner, the operator may move the scan plane of the precursor image in real-time until a desired scan plane(s) for the localizer images are found.

If the operator does not prescribe a new scan plane, then the scan plane of the current precursor image may also be a suitable scan plane for localizer images to be acquired in step 518. However, if there is no indication made by the operator to start acquiring localizer images, then the real-time scanning and updating of the precursor image at window 304 continues with the scan plane positioned at the last specified position (step 508 and the return to step 504).

Otherwise, once the operator specifies a new scan plane (step 506) and is satisfied with the new precursor image corresponding thereto (steps 510 and 512), the operator may be ready to initiate acquisition of localizer images (e.g., step 518). If the operator is still not satisfied with the new scan plane, then he/she may further move the scan plane in real-time (i.e., return to step 506) until the scan plane position of desired localizer images is found via real-time precursor images at window 304.

It is also contemplated that the operator may explicitly stop the real-time scanning and updating of the precursor image before prescribing the new scan plane for the next precursor image in step 506 and/or before acquiring localizer images in step 518. The operator may initiate such a stop by clicking on icon 314 provided on GUI 300.

In step 518, acquisition of localizer images are initiated by the operator, for example, by clicking on icon 316. In one embodiment, a center point on the precursor image (or alternatively, any point on the suitable precursor image that the operator specifies or that is provided as a default by the MR imaging system) is the location (e.g., (x, y, z) coordinate location relative to a reference frame) at which the scan planes of each of the localizer images being acquired will intersect. Three mutually orthogonal 2-D localizer images are acquired and displayed at windows 306–310 (step 520). As discussed above with respect to scheme 400, the relative orientations of the localizer images to each other may vary, and may be preset or may be specified by the operator. Also, more of less than three localizer images may be acquired per a given suitable precursor image. In any case, the location and orientation of scan planes associated with each of the localizer images is relative to the location and orientation of the suitable precursor image. Preferably, the acquisition of the localizer images are interleaved with the updating of the precursor image in real-time.

Viewing the displayed localizer images, if the operator finds such localizer images to be suitable to generate target images therefrom (step 522), then such localizer images may be the basis for prescribing and/or acquiring desired target images (step 524). The scan plane positions of the displayed localizer images may also be the scan plane positions for the desired target images. Alternatively, the displayed localizer images may be the basis for graphical prescription of the scan planes of the target images (e.g., clicking icon 322). The target images may also be displayed on GUI 300 (not shown).

Otherwise, when the displayed localizer images are not suitable to generate target images therefrom (step 522), then the operator prescribes and acquires different localizer images via the precursor image on window 304 (return to step 508). The operator prescribes a new scan plane of the precursor image (step 506) and again makes a determination as to whether this new scan plane is a suitable position at which to acquire the localizer images (step 514). Recall that real-time acquisition and updating of the precursor image on window 304 is continuously occurring even as localizer images and/or target images are being prescribed, acquired, and/or displayed on GUI 300. Hence, the operator is provided with the flexibility to "jump" between (e.g., view and/or manipulate) the different types of images at will within the same environment (e.g., GUI 300), such that timely and precise acquisition of desired target images occur.

In most cases, once localizer images have been acquired, the target images generated therefrom would most likely contain desirable image content (i.e., desired images of a specific region within the subject of interest are being provided). Thus, using scheme 500, successive iterative sets of target images to obtain high resolution desired images of the specific region within the subject of interest would not be required. The searching or maneuvering of a scan plane within the subject of interest to find the specific region desired to be imaged is primarily performed using the precursor images, at much time savings, rather than by using localizer images and/or target images.

In this manner, the overall scan time is decreased, the operator works from a less number of different types of images, the target images most likely contain highly relevant and desirable information, and localizer images are acquired only on an as-needed basis and in real-time (rather than acquiring a plurality of sets of localizer images, some of which may not be at useful locations and/or orientations, from which a certain amount of guessing would still be involved to prescribe target images therefrom).

Note that scheme 400, in contrast to scheme 500, does not require the use of precursor image(s) since prescription of desirable localizer images is based on other localizer images (e.g., localizer images acquired at the landmark position).

Figure 7:
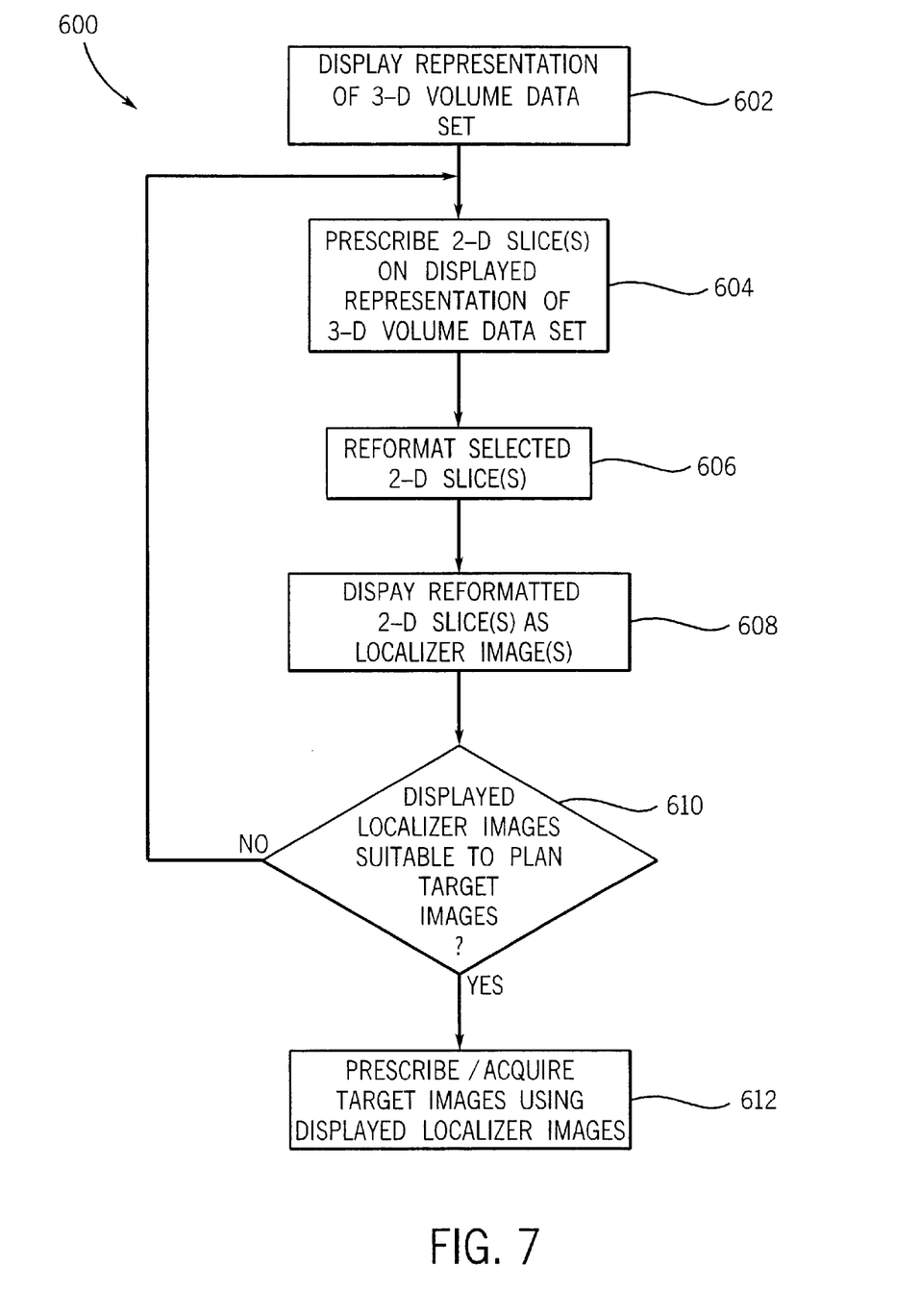
FIG. 7 is a flow diagram showing still another embodiment of the image acquisition scheme included in the MR imaging system of FIG. 1.

Referring to FIG. 7, there is shown a flow diagram of still another embodiment of a "just-in-time" localizer image acquisition scheme 600. Scheme 600 includes a display 3-D representation step 602, a prescribe 2-D slices step 604, a reformat step 606, a display reformatted 2-D slices step 608, a suitability checking step 610, and a target image prescription step 612. Scheme 600 is configured to use acquired data representative of a 3-D volume within the subject of interest to generate just-in-time 2-D localizer images, which in turn are the basis for desirable 2-D target images.

In step 602, data corresponding to an 3-D volume within the subject of interest (this 3-D volume containing the specific region desired to be viewed) is displayed in an GUI such as window 304 of GUI 300. The data has already been acquired by the MR imaging system and is being represented on GUI 300 as an 3-D volume data set. For example, the 3-D volume data set may be graphically represented as a cube having an image on each of its faces, each image being representative of a boundary image of the 3-D volume.

In step 604, the operator prescribes one or more 2-D slices on the representation of the 3-D volume data set. The prescription is performed using graphical prescription tools (as previously discussed). Once prescription is complete, in step 606, the data representative of the selected 2-D slice(s) are reformatted from its 3-D representation to a 2-D representation (i.e., localizer images). In other words, at least a portion of the 3-D volume data set is used to generate or form each of the localizer images, the scan planes of the localizer images being identical to the location and orientation of the 2-D slices prescribed in step 604. As is well-known in the art, reformatting is a process for generating one or more 2-D images from a 3-D volume data set.

In step 608, such reformatted 2-D slices are the 2-D localizer images displayed on windows 306–310. Note that scheme 600 does not acquire additional images or data once the 3-D volume data set has been acquired. Instead, the displayed localizer images are generated using already acquired data comprising the 3-D volume data set. In one embodiment, only a partial amount of the data associated with a given prescribed 2-D slice may be utilized to become its corresponding localizer image. Although this may result in a localizer image having lower resolution than that of the fully reconstructed 2-D slice, the localizer image would be provided in a shorter amount of time and in any case, unlike target images, localizer images need not be of the highest possible resolution.

If the location and orientation of the displayed localizer image are suitable (step 610), then target images may be prescribed and/or be generated relative to the location and orientation of one or more localizer images (step 612). Target images are acquired through a conventional 2-D scanning process (similar to the target image acquisition in scheme 400 or 500). Otherwise, if the displayed localizer images are not at a desired location and orientation, then new 2-D slices (i.e., localizer images) may be prescribed (return to step 604).

Alternatively, target images may also comprise 2-D slices from the 3-D volume data set. To achieve the highest possible resolution, all of the data associated with a given 2-D slice would be used in the reformatting process to generate the corresponding target image.

Just-in-time image acquisition schemes for imaging in a single area of the subject of interest (such as schemes 400, 500, or 600) can be applied for imaging multiple (adjacent) areas (also referred to as sections or stations) of the subject of interest, including localizer image prescription and acquisition, target image prescription from localizer images, and target image acquisition. Multiple areas of the subject of interest may be imaged in successive order by moving the table and the patient relative to the MR imaging system one or more times during a given scanning session.

Figure 8A:
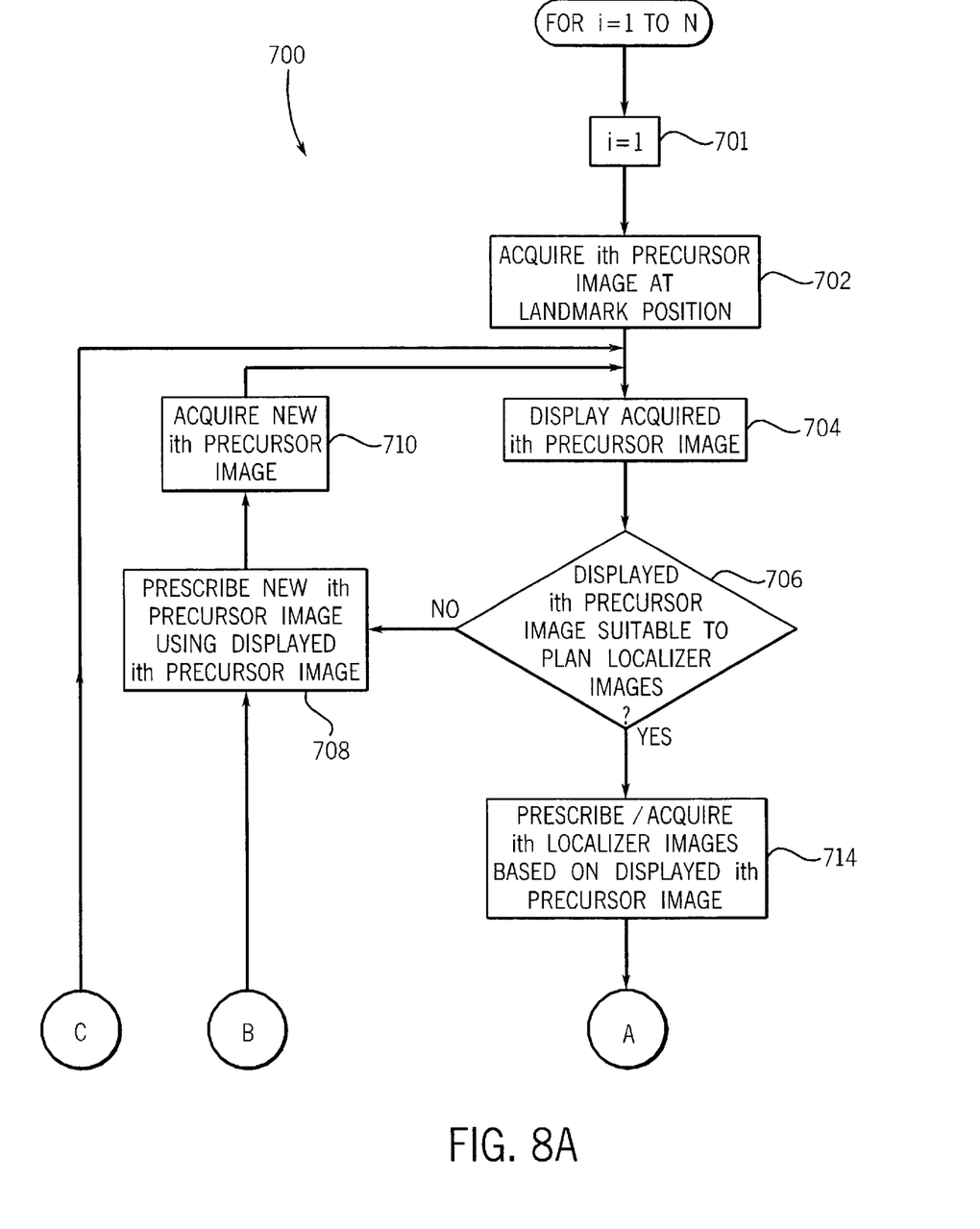
FIGS. 8A–8B are flow diagrams showing yet another embodiment of the image acquisition scheme included in the MR imaging system of FIG. 1.
Figure 8B:
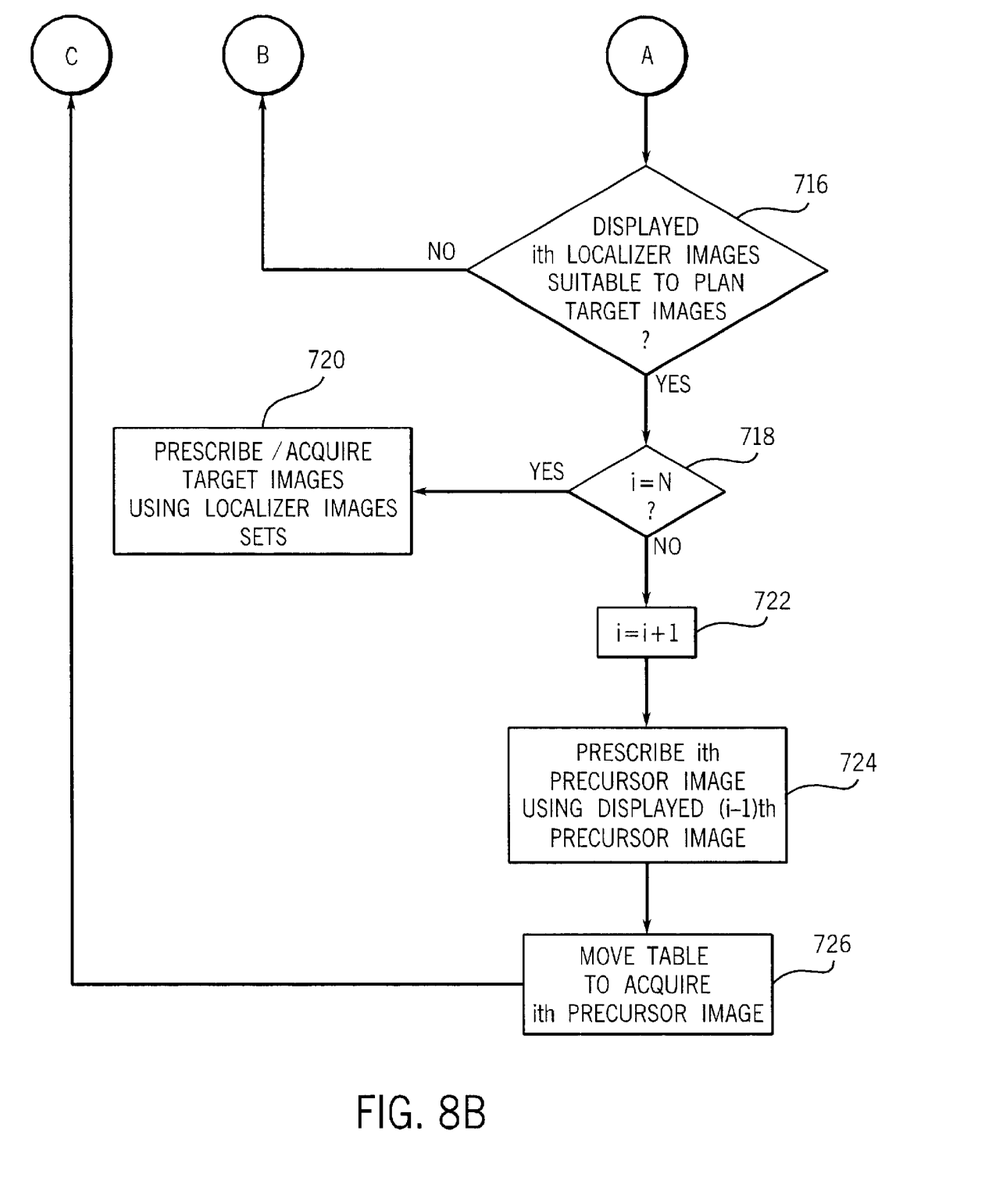

Referring to FIGS. 8A–8B, there is shown flow diagrams of an alternative embodiment of a "just-in-time" localizer image acquisition scheme 700. Scheme 700 is configured to acquire just-in-time localizer images in an MR imaging system configured for table movement during a scanning session. Table movement is desirable when imaging a relatively large area of the subject of interest, such as, the vasculature of a patient's legs, to ensure that the magnet isocenter (where the main magnetic field ($B_0$) is the most homogenous) is aligned with each part of the large area being imaged. In other words, the table with the patient positioned thereon will move relative to the magnet isocenter after images for a given area have been acquired so that the magnet isocenter is always aligned with the current section or station of the large area to be imaged. Accordingly, each station of the large area of the subject of interest will be associated with a unique precursor image, localizer images, and target images.

For i=1 to N, where N= the number of sections of the large area being imaged (e.g., N=3 in GUI 302), a continuously updating precursor image, acquisition of localizer images relative to the precursor image, and acquisition of target images relative to the localizer images as described in scheme 500 similarly occurs for each ith section in scheme 700. For i=1 (step 701), a precursor image for the ith section being imaged is acquired at a landmark position (step 702). Such precursor image is displayed at one of windows 324, 326, 328 (e.g., since i=1, displayed at window 324).

When a suitable ith precursor image has been identified, prescription and/or acquisition of an ith localizer images set occurs based on the ith suitable precursor image (step 714). Such ith localizer images set is displayed at windows 330. The scan planes of the ith localizer images set are related to the suitable ith precursor image (as discussed for scheme 500). Otherwise, a new scan plane for the next precursor image is prescribed using the current ith precursor image (step 708) and the next precursor image is acquired (step 710) and displayed at window 324 (step 704).

In step 716, if the ith localizer images set are not suitably positioned from which to prescribe or acquire ith target images from, then a new ith precursor image is acquired (return to step 708). Alternatively, although not shown, a new ith localizer images set may be prescribed from the current ith localizer images set using appropriate prescription tools.

If i=N (step 718), then all useful or suitable localizer images for all N sections have been generated and target images for each section may be prescribed and/or acquired in GUI 302, using identical scan planes as its respective localizer images (step 720). If i<N, then i is indexed by 1 (i=i+1 in step 722) and a precursor image for the next section to be imaged (to be displayed at window 326) may be prescribed relative to the precursor image for the previous section (e.g., the image at window 324 (step 724)). Alternatively, the precursor image at window 326 may be acquired at a landmark position.

In step 726, the table is moved to align the magnet isocenter with this next section of the large area. Then images of this next section can be acquired, including the precursor image that has been prescribed, in one manner or another, in step 724. Once the table movement is complete, the precursor image can be acquired and displayed at window 326 (return to step 704). This looping in scheme 700 occurs a plurality of times until desirable localizer images for all N sections have been provided to the operator via GUI 302.

While the embodiments and application of the invention illustrated in the figures and described above are presently preferred, it should be understood that these embodiments are offered by way of example only. For example, the localizer or localizer image acquisition schemes described above are also applicable in other types of imaging systems, such as, computerized tomography (CT) systems. Accordingly, the present invention is not limited to a particular embodiment, but extend to various modifications that nevertheless fall within the scope of the appended claims.

What is claimed is:

1. A method for generating a clinically useful image having a desired image acquisition plane in a short time frame, the method comprising the steps of:
    prescribing a second image relative to at least one of a default second image, a first image, and a representation of a three-dimensional volume data set;
    acquiring the second image;
    displaying the second image;
    prescribing the clinically useful image relative to the second image;
    acquiring the clinically useful image; and
    displaying the clinically useful image,
    wherein the second image and the clinically useful image are prescribed, acquired, and displayed within a single graphical prescription environment included in an imaging system.

2. The method of claim 1, wherein the default second image is an image acquired at an operator specified default location and orientation within an object of interest or at a landmark position within the object of interest.

3. The method of claim 1, wherein an image resolution associated with the clinically useful image is greater than an image resolution associated with the second image.

4. The method of claim 3, wherein the image resolution associated with the second image is greater than an image resolution associated with the first image.

5. The method of claim 1, wherein the first image is an image acquired in real-time and updated continuously within the single graphical prescription environment.

6. The method of claim 1, wherein the acquisition of the second image and the first image are interleaved with each other.

7. The method of claim 1, wherein prescribing a second image includes prescribing a localization image acquisition plane associated with the second image.

8. The method of claim 7, wherein prescribing the clinically useful image includes prescribing the desired image acquisition plane of the clinically useful image, wherein the desired image acquisition plane and the localization image acquisition plane are identical to each other.

9. The method of claim 1, further comprising acquiring a plurality of second images based on the first image, the first image including a point and a plurality of image acquisition planes being associated with the plurality of second images.

10. The method of claim 9, wherein the point on the first image is an intersection point of the plurality of image acquisition planes associated with the plurality of second images.

11. The method of claim 9, wherein at least one of the image acquisition planes is non-intersecting with respect to another of the image acquisition planes.

12. The method of claim 1, wherein prescribing a second image includes prescribing a two-dimensional slice within the representation of the three-dimensional volume data set.

13. The method of claim 12, wherein acquiring the second image includes reformatting the two-dimensional slice, the reformatted two-dimensional slice being the second image.

14. An imaging system for generating a clinically useful image having a desired image acquisition plane in a short time frame, the system comprising:

means for prescribing a second image relative to at least one of a default second image, a first image, and a representation of a three-dimensional volume data set;

means for acquiring the second image;

means for displaying the second image;

means for prescribing the clinically useful image relative to the second image;

means for acquiring the clinically useful image; and means for displaying the clinically useful image, wherein the second image and the clinically useful image are prescribed, acquired, and displayed within a single graphical prescription environment included in the imaging system.

15. The system of claim 14, wherein the default second image is an image acquired at an operator specified default location and orientation within an object of interest or at a landmark position within the object of interest.

16. The system of claim 14, wherein an image resolution associated with the clinically useful image is greater than an image resolution associated with the second image.

17. The system of claim 16, wherein the image resolution associated with the second image is greater than an image resolution associated with the first image.

18. The system of claim 14, wherein the first image is an image acquired in real-time and updated continuously within the single graphical prescription environment.

19. The system of claim 14, wherein acquisition of the second image and the first image are interleaved with each other.

20. The system of claim 14, wherein the means for prescribing a second image is configured to prescribe a localization image acquisition plane associated with the second image.

21. The system of claim 20, wherein the means for prescribing the clinically useful image is configured to prescribe the desired image acquisition plane of the clinically useful image, wherein the desired image acquisition plane and the localization image acquisition plane are identical to each other.

22. The system of claim 14, further comprising means for acquiring a plurality of second images based on the first image, the first image including a point and a plurality of image acquisition planes being associated with the plurality of second images.

23. The system of claim 22, wherein the point on the first image is an intersection point of the plurality of image acquisition planes associated with the plurality of second images.

24. The system of claim 22, wherein at least one of the image acquisition planes is non-intersecting with respect to another of the image acquisition planes.

25. The system of claim 14, wherein the means for prescribing a second image is configured to prescribe a two-dimensional slice within the representation of the three-dimensional volume data set.

26. The system of claim 25, wherein the means for acquiring the second image is configured to reformat the two-dimensional slice, the reformatted two-dimensional slice being the second image.

* * * * *